United States Patent
Ryabova et al.

(10) Patent No.: US 9,453,008 B2
(45) Date of Patent: Sep. 27, 2016

(54) ANTITHROMBOTIC AND ANTIATHEROSCLEROTIC AGENT AND METHOD FOR PRODUCING SAME (VARIANTS)

(71) Applicant: PROTON OOO, Tomsk (RU)

(72) Inventors: Svetlana Yurevna Ryabova, Moscow (RU); Valery Aleksandrovich Parshin, Moscow (RU); Vladimir Grigorevich Granik, Moscow (RU); Nikita Borisovich Grigoriev, Moscow (RU); Ludmila Mikhaylovna Alekseeva, Moscow (RU)

(73) Assignee: PROTON OOO, Tomsk (RU)

( * ) Notice: Subject to any disclaimer, the term of this patent is extended or adjusted under 35 U.S.C. 154(b) by 55 days.

(21) Appl. No.: 14/344,032

(22) PCT Filed: Oct. 29, 2012

(86) PCT No.: PCT/RU2012/000884
§ 371 (c)(1),
(2) Date: Mar. 10, 2014

(87) PCT Pub. No.: WO2013/070116
PCT Pub. Date: May 16, 2013

(65) Prior Publication Data
US 2014/0235868 A1    Aug. 21, 2014

(30) Foreign Application Priority Data
Nov. 8, 2011 (RU) .................................. 2011144895

(51) Int. Cl.
*C07D 413/06* (2006.01)
*A61K 31/422* (2006.01)
*A61P 7/02* (2006.01)
*A61P 9/00* (2006.01)

(52) U.S. Cl.
CPC .................................. *C07D 413/06* (2013.01)

(58) Field of Classification Search
USPC ........................................................ 548/215
See application file for complete search history.

(56) References Cited

FOREIGN PATENT DOCUMENTS

RU    2008308 C1    2/1994
RU    2026287 C1    1/1995

OTHER PUBLICATIONS

Ryabova et al. "Synthesis and Transamination of Indoxyls and Pyrrol-2-In.4-Ones." S.Ordzhonikze All-Union Research Institute for Pharmaceutical Chemistry, Moscow 119021. Translated from Khimiya Geterotsiklicheskikh Soedinenii, No. 11, pp. 1487-1494, Nov. 1990. Original article submitted Apr. 20, 1989.
Ryabova et al. "Acylation of Enamino Ketones of the Indolin-3-One and 2-Pyrrolin.4-One Series and Synthesis of 2-Indolyland 5-Pyrrolyiacrylic Acid Derivatives." S. Ordzhonikidze Au-Union Scientific Research Pharmaceutical Chemistry Institute, Moscow 119021. Translated from Khimiya Geterotsiklicheskikh Soedinenii, No. 3, pp. 343-348, Mar. 1991. Original article submitted May 30, 1989.
Ryabova et al. "Synthesis and Biological Activity of Dienediaminoketones of the Indolin-3-One and 2-Pyrrolin-4-One Series." Translated from Khimiko-Farmatsevticheskii Zhurnal, vol. 29, No. 9, pp. 22 -29, Sep. 1995. Original article submitted Jun. 7, 1995.
Khmelnitskaya et al. "Study of Oxidation—Reduction Properties and No-Donor Ability of Dienediamines in the Indole, Pyrrole, and Thiophene Series." Translated from Khimiya Geterotsiklicheskikh Soedinenii, Chemistry of Heterocyclic Compounds, vol. 38, No. 11, 2002. Original article submitted Mar. 21, 2000.
Feelisch. "The Biochemical Pathways of Nitric Oxide Formation from Nitrovasodilators: Appropriate Choice of Exogens NO Donors and Aspects of Preparation and Handling of Aqueous NO Solutions." Journal of Cardiovascular Pharmacology. 17 (Suppl. 3):525-533, Raven Press, Ltd., New York, 1991.
Hansson. "Immune Mechanisms in Atherosclerosis." Arteriosclerosis, Thrombosis, and Vascular Biology Journal of the American Heart Association, 2001; 21:1876-1890.
Orekhov et al. "The Effects of Antihypertensive Agents on Atherosclerosis-Related Parameters of Human Aorta Intimal Cells." Cardiology 1998; 89:111-118.
Zadelaar et al. "Mouse Models for Atherosclerosis and Pharmaceutical Modifiers." Arteriosclerosis, Thrombosis, and Vascular Biology Journal of the American Heart Association, 2007; 27; 1706-1721; originally published online May 31, 2007.
International Search Report dated Apr. 25, 2013, in corresponding PCT application No. PCT/RU2012/000884.
BD ACS on STN, Apr. 6, 2002, jointure with RN 425399-08-2.

*Primary Examiner* — Joseph Kosack
*Assistant Examiner* — Amanda L Aguirre
(74) *Attorney, Agent, or Firm* — Dergosits & Noah LLP (57) ABSTRACT

The invention relates to the field of chemical and pharmaceutical industry and medicine and concerns compounds which can be used to produce agents for the treatment of cardiovascular diseases.
The use of 2-[2-cyano-2-[5-(hydroxymethyl)-3-methyl-1,3-oxazolidin-2-ylidene]ethylidene]indolin-3-one of formula I is proposed as a biologically active compound exhibiting the properties of exogenous nitric oxide donor, a platelet aggregation inhibitor, also exhibiting antihypertensive activity and activating activity towards the soluble guanylate cyclase enzyme. Variants of methods for synthesizing the above compound are also proposed.

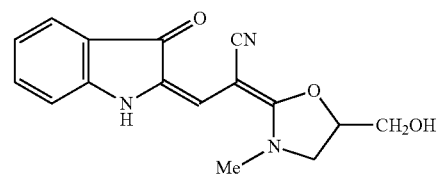

2 Claims, 3 Drawing Sheets

Figure 1 – The effect of the compound I and sodium nitroprusside on ADP-induced platelet aggregation following intravenous administration in rabbits (% compared to control).

Figure 2 - Changes in platelet functional activity following peroral administration of the compound I in a model of ADP-induced aggregation in rabbits (% compared to control).

Figure 3 – Changes in platelet aggregation, induced by arachidonic acid, following peroral administration of the compound I in rabbits (% compared to control).

ANTITHROMBOTIC AND ANTIATHEROSCLEROTIC AGENT AND METHOD FOR PRODUCING SAME (VARIANTS)

CROSS-REFERENCE TO RELATED APPLICATION

This application is a U.S. National Phase of International Application No. PCT/RU2012/000884 filed on Oct. 29, 2012, which claims priority to and the benefit of Russian Patent Application No. 2011144895 filed on Nov. 8, 2011, the entire contents of which are incorporated herein by reference.

FIELD OF THE INVENTION

The invention relates to the field of chemical and pharmaceutical industry and medicine and concerns compounds which can be used to produce agents for the treatment of cardiovascular diseases.

BACKGROUND OF THE INVENTION

Cardiovascular diseases remain the leading cause of human mortality, one of the most significant causes of this phenomenon is atherosclerosis and high blood level of low-density lipoproteins. Atherosclerosis is a chronic cardiovascular disease in which an artery wall thickens as a result of connective tissue growth, formation of atherosclerotic plaques, lumen narrowing and tissue ischemia.

Abnormal regulation of cholesterol production causes severe pathologies. When total cholesterol production (synthesized and ingested cholesterol) exceeds the amount, necessary for construction and repair of membranes and generation of bile acids and steroids, the accumulation of cholesterol in vessels (atheromatosis) can cause vascular occlusion (atherothrombosis). Cardiovascular pathology is caused by high cholesterol level and especially by high level of low-density lipoproteins (LDL).

The modern opinion on atherosclerosis is that it is a chronic inflammatory disease. Therefore, anti-inflammatory drugs like aspirin, which also has antiplatelet properties, as well as angiotensin-converting-enzyme inhibitors and anti-inflammatory cytokines, are useful for patients suffering from atherosclerosis.

Hypertension is often associated with atherosclerotic damage of vascular wall and, therefore, research, aimed at studying the effect of antihypertensive drugs on the development of atherosclerosis, is important. According to some studies, calcium antagonists have anti-atherogenic properties, as evidenced by the prevention of atherosclerotic damage manifestation. Angiotensin-converting-enzyme inhibitors also exert anti-atherogenic effect in animal experiments. Calcium antagonists verapamil and amlodipine exert anti-atherogenic effect, suppressing serum-induced cellular proliferation, protein synthesis and cholesterol accumulation in cells. Both drugs reduce the severity of atherosclerosis, exhibiting anti-atherosclerotic and anti-atherogenic activity in cell culture. On the contrary, perindopril does not affect atherosclerotic parameters while propranolol even stimulates cholesterol accumulation, proliferative activity of cells and protein synthesis. According to some authors [9], data, obtained using cell cultures, can reflect the in vivo situation. Studies of patients with coronary atherosclerosis treated with calcium antagonists or propranolol have shown, that the latter inhibits atherogenesis to a degree in these conditions. Based on the performed research the authors have made the following ranking of efficacy of the examined drugs: amlodipine>verapamil>perindopril>propranolol.

Among drugs, widely used for treating atherosclerosis, are statins, such as lovastatin, simvastatin, pravastatin, atorvastatin, fluvastatin.

It is important to note, that the mechanism of action of statins is associated with inhibiting a speed-limiting stage of cholesterol biosynthesis—conversion of β-hydroxy-β-methyl-glutaryl-CoA (HMG-CoA) to mevalonate, which is catalyzed by the enzyme HMG-CoA reductase.

Research [10] has shown that, despite the success of statin use in effectively reducing cholesterol levels and reducing mortality in cardiovascular diseases, damage of coronary vessels was still observed in about two thirds of patients treated with statins.

Another promising venue of atherosclerosis treatment, besides, for example, raising the level of high-density lipids, is an inhibition of systemic and vascular inflammation process [8].

Currently, combinations of drugs are used to treat atherosclerosis, because monotherapy is not possible. The main reason of this is the absence of a compound, possessing the most optimal spectrum of pharmacological activity: anti-inflammatory, antiplatelet, antihypertensive and hypocholesterolemic. The search for such a molecule is an important goal of pharmacology.

During the last 15 years the understanding of the functioning of different biological systems has changed. It was discovered that nitric oxide (NO), a low-molecular compound, is one of the universal and necessary regulators of cellular metabolism functions. Nitric oxide participates in regulating vascular tone, inhibits platelet aggregation and adhesion on blood vessel walls, and is involved in central and vegetative nervous system, regulating the activity of respiratory organs, gastrointestinal tract and urinary system. Nitric oxide plays an important role in neurotransmission, immune system regulation and protection of the organism from bacterial infections.

Nitric oxide is known to be a potent inhibitor of platelet aggregation. Nitric oxide generation preserves the blood flow by inhibiting thrombogenesis. Factors, regulating the generation and utilization of NO in endogenous conditions, are important in ensuring normal functioning of the cardiovascular system.

In light of the abovementioned, it is important for modern pharmacology to find compounds, able to stimulate the production of nitric oxide as an agent, that inhibits spontaneous and induced platelet aggregation. Thus, in the present study, the search for new effective compounds, which may be useful in medical practice, is based on synthesis and biological research of new nitric oxide generators, which are not structurally analogous to the known NO donors.

Some compounds in indolinone-3 series are known to have antihypertensive activity [2, 4, 5, 6] and being able to generate nitric oxide [1], but there are no compounds in this series, known to be able to activate the soluble guanylate cyclase enzyme and exert antiplatelet action.

SUMMARY OF THE INVENTION

The goal of the invention is the use of a derivative of indolinone-3 as a biologically active compound that can be used to produce a drug for treating cardiovascular diseases.

The goal is achieved by using a compound, exhibiting the properties of exogenous nitric oxide donor, activator of soluble guanylate cyclase enzyme, platelet aggregation inhibitor and exhibiting antihypertensive activity.

The present invention relates to compounds of indolinone-3 series, specifically, a new derivative of this series -a 2[2-cyano-2-[5-(hydroxymethyl)-3-methyl-1,3-oxazolidin-2-ylidene]ethylidene]indolin-3-one of formula I:

DETAILED DESCRIPTION OF THE INVENTION

Research of antiplatelet properties of the compound I, its effect on the activity of soluble guanylate cyclase and NO generation was performed by experimentation in vitro, its ability to exert hypotensive and antihypertensive action was studied on animals. General toxicity and tolerability of the compound of formula I were studied on animals.

Studies have shown that the compounds exhibit potent antiplatelet activity, releases NO and potently activates soluble guanylate cyclase.

EXAMPLE 1

Antiplatelet activity was assessed by the effect of the compound on platelet aggregation of rabbit blood plasma, induced by ADP (adenosine diphosphate) and arachidonic acid. Platelet aggregation was assessed by the change of optical density of plasma. Studies were performed using both intravenous administration, in comparison with sodium nitroprusside, and oral administration, in comparison with acetylsalicylic acid. Compound I was used in concentrations of $10^{-3}$-$10^{-7}$ M (parenteral administration) and in 4-8 and 12 mg/kg doses (oral administration).

Experiments have shown, that the compound of formula I significantly inhibits ADP-induced platelet aggregation.

In order to make a final conclusion on the ability of the studied compound to inhibit platelet aggregation experiments were performed in conditions of living organism using intravenous and oral administration.

Figure 1:
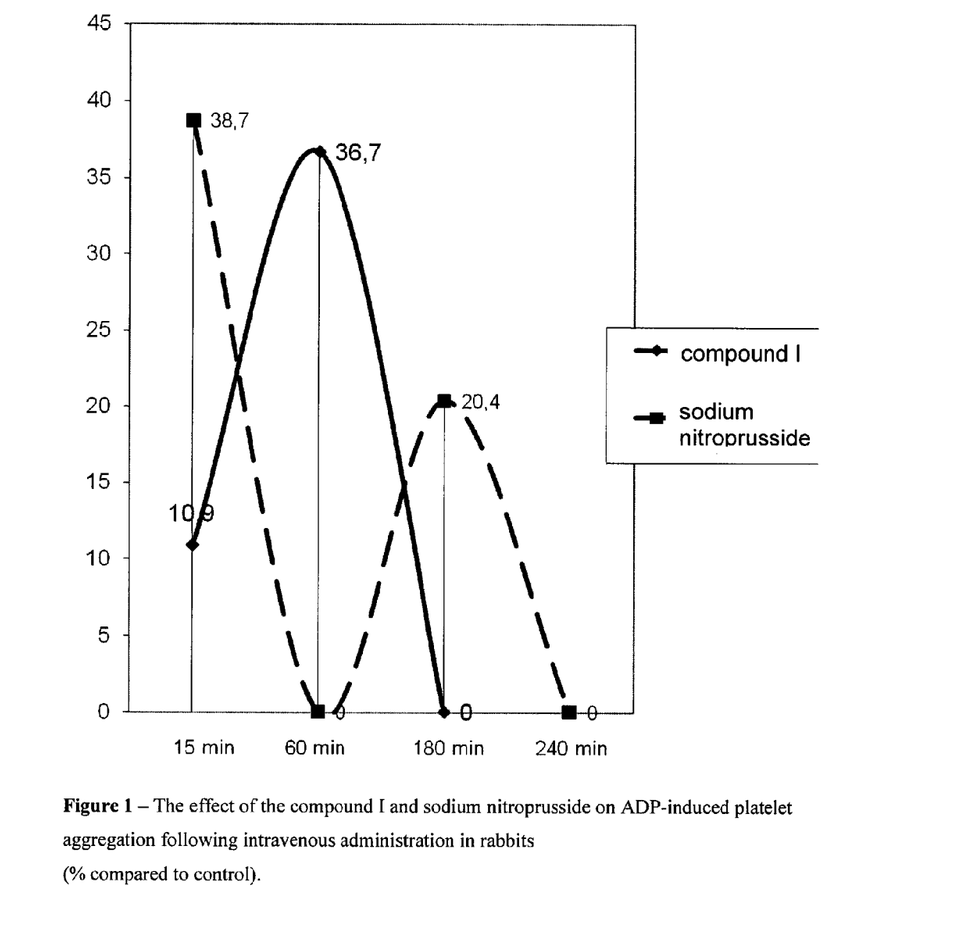
FIG. 1 is a graph showing the effect of the compound I and sodium nitroprusside on ADP-induced platelet aggregation following intravenous administration in rabbits (% compared to control).

Compound I and sodium nitroprusside (a reference drug) have both inhibited the process of platelet aggregation. However, there were considerable quantitative and temporal differences in their effects. Sodium nitroprusside potently inhibited platelet aggregation 15 minutes after the administration. This was the only time point where we managed to observe its activity. After 1 hour the effect disappeared. Inhibition of platelet aggregation, caused by compound I, was too observed 15 minutes after the administration (as a tendency), achieved maximal potency after 60 minutes and stopped at the $3^{rd}$ hour of the experiment (FIG. 1).

Thus, these experiments have shown the ability of the compound of formula I to inhibit ADP-induced platelet aggregation after intravenous administration.

Figure 2:
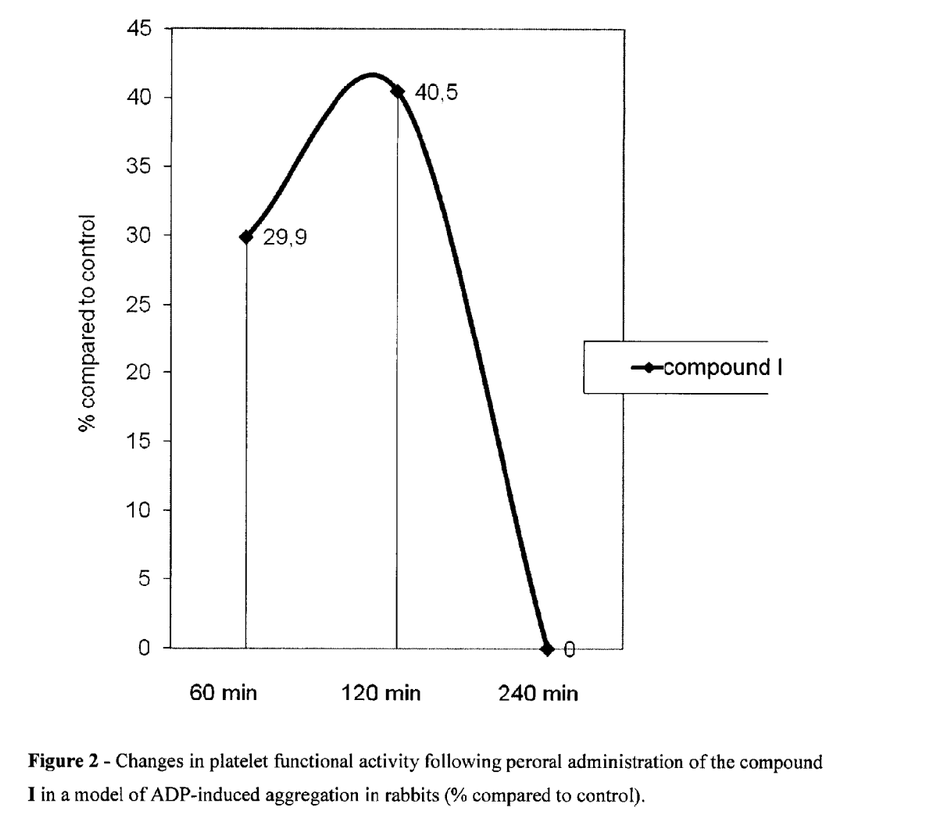
FIG. 2 is a graph showing the changes in platelet functional activity following peroral administration of the compound I in a model of ADP-induced aggregation in rabbits (% compared to control).

Considerable inhibition of the process of ADP-induced aggregation was noted after the first hour (30%), achieved maximal potency after 2 hours (40%) and persisted, as a tendency (15-25%), for all 4 hours of observation (FIG. 2).

Using arachidonic acid (AA) as an aggregation inductor, the experiments were performed in conditions of oral administration. We consider such experimentation justified by the possibility of different routes of administration for the tested compound, not only intravenous one (unlike sodium nitroprusside).

Figure 3:
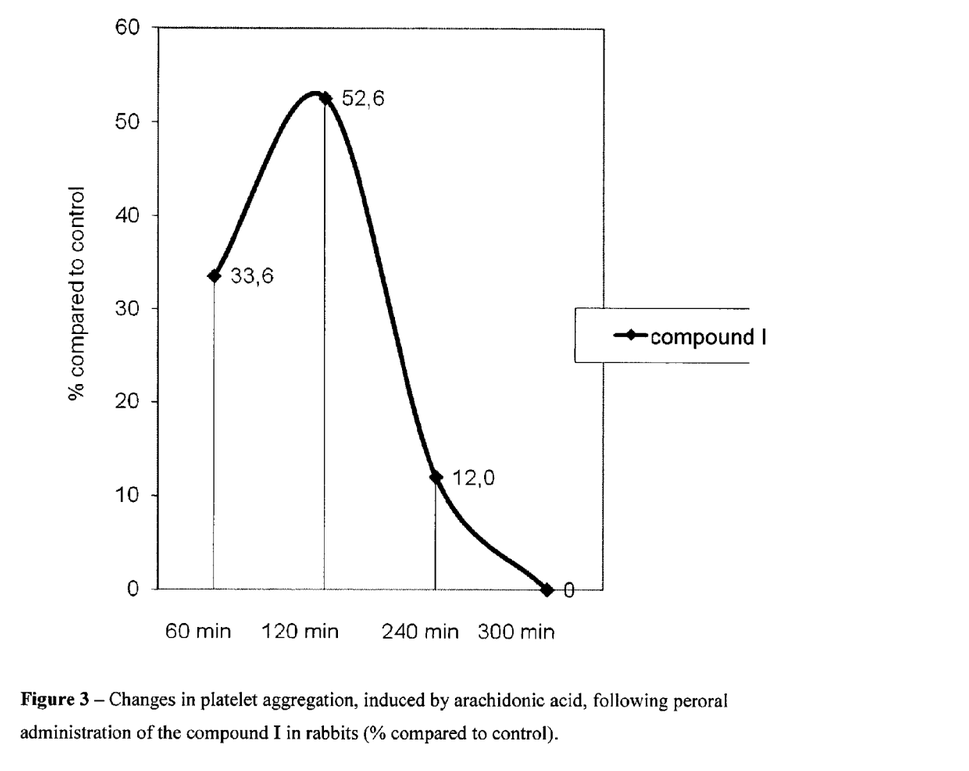
FIG. 3 is a graph showing the changes in platelet aggregation, induced by arachidonic acid, following peroral administration of the compound I in rabbits (% compared to control).

It was noted that the compound of formula I starts to act 1 hour after the administration, the potency of platelet aggregation induced by arachidonic acid was reduced by a third. The action of the inductor (AA) was even more inhibited after 2 hour—by over two times. At the end of the observation period (4 hours) the action of AA was comparable to the control (FIG. 3).

The effect of the compound of formula I persisted for over 4 hours. Qualitatively it was detected as a tendency (up to 10%) at the end of the first hour, became statistically significant after 2 hours (32%) and continued to increase for the whole observation period (38% at 4 hour).

Thus, platelet aggregation, induced by AA, was effectively inhibited by the compound of formula I, administered per os, and the activity persisted for over two hours.

We have also studied the effect of the compound on formylmethionyl-leucyl-phenylalanine (FMLP)—induced generation of superoxide anion radical ($O_2^-$.) by human neutrophils, weakened by pathological processes (histiocytosis, stage 2 hypertension). Such experimentation was chosen due to the fact, that, in order to perform a complete phagocytosis with complete destruction of pathogenic microorganisms, phagocytes, including neutrophils, generate the so-called reactive oxygen species (ROS), including oxygen radicals and compounds easily converting into such radicals. Superoxide anion radical ($O_2^-$.) hydroxyl radical (OH.) and lipid hydroxyperoxides (ROO*) also belong to AOF. All these compounds have one unpaired electron on outer molecular orbital, giving them high reactivity, which causes their interaction with cell molecules: proteins, RNA, DNA, etc, accompanied by the loss of their biological activity.

It should be noted, that besides having protective functions (inactivation of bacterial toxins) oxygen radicals (at long action) often have damaging effect of surrounding cells, leading even to their death. Because of this, the search for chemical compounds, briefly enhancing ROS generation or inhibiting this process, is an important task of modern pharmacology.

After the interaction of the compound of formula I with whole blood, the interaction of NO with $O_2^-$. results in a highly reactive compound peroxynitrite (ONOO.), which, presumably, effectively affects the lipid components of cellular cytoplasmic membrane, including AA residue.

Due to this, possibly, the release of AA from the phospholipid layer of plasma membranes is disrupted, as well as its subsequent metabolism with the generation of thromboxane $A_2$ ($TxA_2$) in platelets, reducing the functional activity of platelets. Thromboxane $A_2$, as it is well known, is a potent endogenous vasoconstrictor and proaggregant.

The obtained data allows us to suppose, that one of the possible mechanisms of antiplatelet action of the compound of formula I may be the activation of the process of generation of oxygen radicals in whole blood, which allows to reduce the level of thrombogenic factors.

The model of parenchymal hemorrhage characterizes hemostasis through the stimulation of coagulation cascade. Usually, it is rather difficult to obtain considerable change of bleeding time in these models with resorptive-acting compounds. Direct-action anticoagulants (heparin, heparinoids) prolong bleeding time in these models only in high doses, while the effect is detected at different time (up to 3 hours after the administration). Indirect-action antiplatelet drugs (oxycoumarines, indandiones, etc.) usually begin to increase bleeding after a certain delay period (12-48 hours after the administration), which is easily explainable by the modern understanding of their mechanism of action: they stop the biosynthesis of blood clotting plasma factors II, VII, IX, X, while the duration of delay period is determined by the amount of these factors, produced in the liver before the administration of vitamin K reductase inhibitors (oxycoumarines, indandiones).

The duration of parenchymal hemorrhage in the control group was 88.9±1.2 s. Test groups of animals used in the experiments 60 minutes after oral administration of the compound of formula I. After the administration of 8 mg/kg dose the duration of parenchymal hemorrhage in test group increased by 71% compared to original condition, it further increased to 220.6±3.4 s after another hour. This parameter did not differ from the control group at the end of experiment (240 min). The duration of bleeding was increased twofold after a 16 mg/kg dose and was registered only in the first 60 min of the observation.

The discovered effect, it seems, can be explained by an earlier discovered ability of the compound of formula I to inhibit the platelet part of hemostasis, which is realized through NO generation, regulation of intracellular calcium level in platelets, etc.

Another fact, which makes the new compound promising, is its high $LD_{50}$ index (8900 mg/kg), corresponding to the V toxicity class—practically nontoxic compounds.

Summing up the aforementioned (taking into account the performed experiments, that have shown the ability of NO donors to inhibit induced aggregation of platelets) it can be stated that the new compound of formula I potently inhibits platelet aggregation in rabbit organism following parenteral (intravenous) administration.

It is proven that the new NO donor (compound I) can be absorbed from gastrointestinal tract and exert its antiplatelet activity in enteral administration. Certainly, it manifests somewhat later compared to intravenous administration, but persists for a considerably longer period (the compound affected AA-induced aggregation for over 2-4 hours and ADP-induced aggregation for about 3 hours).

Results of the Studies

1. In vitro antiplatelet activity of the newly synthesized nitric oxide donor—the compound of formula I—is as good as that of acetylsalicylic acid.
2. The potential antiplatelet drug, diendiamine of indole series (the compound of formula I), considerably inhibits induced functional activity of platelets after intravenous administration to rabbits. The effect is as potent as that of sodium nitroprusside, but persists for a longer time.
3. The compound of formula I inhibits the action of ADP on platelets following oral administration.
4. The compound of formula I inhibits the action of arachidonic acid on platelet activity.
5. The potential antiplatelet drug—the compound of formula I—briefly enhances the reduced ability of human neutrophils to generate reactive oxygen species.
6. The compound of formula I statistically significantly slows down rat hemostasis in the model of parenchymal hemorrhage, the effect is not dose-dependent.
7. The potential drug (the compound of formula I) belong to the V toxicity class—practically nontoxic.

EXAMPLE 2

The effect of the compound of formula I on hemodynamic parameters, in particular, on systolic arterial pressure (SAP), as well as on the activity of soluble guanylate cyclase and NO generation in in vitro experiments is no less prominent and specific.

The experiments were performed on spontaneously hypertensive (SHT) and normotensive (NT) narcotized male rats using intravenous administration of the tested compounds. The ability of the compound to reduce arterial blood pressure (BP) in SHT rats and prevent spasmogenic reactions to noradrenalin (NA) and angiotensin I (AI).

The compound of formula I was used as a solution in 3% aqueous DMSO. Sodium nitroprusside and nitroglycerin were used as reference drugs.

The administration of the compound of formula I in dose range 0.01-0.1-0.5 and 1.0 mg/kg has exerted dose-dependent antihypertensive effect ranging in time from 30-40 s to 60 min and more. Minimal and short-term hypotensive activity was observed in 0.01 mg/kg dose (reduction of BP by 10-12 mmHg for 30 sec), maximal effect was observed in 1.0 mg/kg dose (reduction of BP by 25-30 mmHg for 60 min).

The reference drug sodium nitroprusside has caused the reduction of BP, similar to the maximal effect of the compound I (reduction of BP by 25 mmHg), in 0.5 mg/kg dose for 20-30 minutes. The effect of 0.01 mg/kg dose of nitroglycerin was similar to that of the tested compound (reduction of BP by 10-15 mmHg for 30-40 s), while in higher doses the reduction of BP did not exceed 20-25 mmHg with duration of 5-6 min (Table 1).

TABLE 1

The effect of the compound of formula I on blood pressure in SHT rats compared to sodium nitroprusside and nitroglycerin

| Tested compound | Dose, mg/kg, intravenously | Reduction of BP, mmHg (Δ) | | | | |
|---|---|---|---|---|---|---|
| | | 10-20 s | 5 min | 30 min | 60 min | 120 min |
| Compound I | 0.01 | −12 ± 5* | — | — | — | — |
| | 0.1 | −15 ± 5* | −20 ± 7* | — | — | — |
| | 0.5 | −10 ± 3* | −20 ± 8* | −25 ± 8* | −30 ± 7* | — |
| | 1.0 | −12 ± 3* | −25 ± 7* | −30 ± 7* | −30 ± 8* | −30 ± 8* |

TABLE 1-continued

The effect of the compound of formula I on blood pressure in
SHT rats compared to sodium nitroprusside and nitroglycerin

| Tested compound | Dose, mg/kg, intravenously | Reduction of BP, mmHg (Δ) | | | | |
|---|---|---|---|---|---|---|
| | | 10-20 s | 5 min | 30 min | 60 min | 120 min |
| Sodium nitroprusside | 0.01 | −5 | −10 ± 3* | — | — | — |
| | 0.5 | −10 ± 3* | −25 ± 5* | −30 ± 8* | −10 ± 3* | — |
| Nitroglycerin | 0.01 | −5 | −10 ± 3* | −3 | — | — |
| | 0.1 | −7 ± 3 | −20 ± 5* | −5 | — | — |
| | 0.5 | −12 ± 3* | −25 ± 7* | −5 | — | — |
| | 1.0 | −10 ± 3* | −25 ± 8* | −7 ± 3 | — | — |

*the difference from base level is significant at $P < 0.05$
— - absence of effect The effects of the compound of formula I on the pressor effects of noradrenaline (NA, 10-15 μg/kg), mesatonum (M, 5 μg/kg) and angiotensin (AI, 5 μg/kg) were studied on normotensive narcotized mice. Antihypertensive action of the compound of formula I was assessed relative to the pressor effects of the control administration of the aforementioned compounds.

As experiments have shown (Table 2), the compound of formula I in dose range 0.01-1.0 mg/kg dose dependently antagonizes the vasoconstrictor effect of NA. The administration of the compound in 0.01 and 1 mg/kg doses the pressor effect of NA reduces by 25 and 50%, and does not significantly change with further dosage increase.

The compound of formula I in aforementioned doses does not significantly affect the pressor action of M, however it does inhibit the pressor effect of AI by 25% in 0.1 mg/kg dose.

Thus, the compound of formula I effectively and dose-dependently reduced BP in spontaneously hypertensive animals, being more potent than the well-known drug sodium nitroprusside. The compound also effectively antagonizes the effects of pressor amines on SAP, which is an evidence of its specific action on the regulation of arterial blood pressure.

TABLE 2

The effect of the compound of formula I on pressor
effects of NA and AI after intravenous administration
in normotensive narcotized rats.

| Compound | Dose, mg/kg | Inhibition of pressor reaction (%) induced by | |
|---|---|---|---|
| | | Noradrenaline | Angiotensin I |
| Compound of formula I | 0.01 | 25 | 0 |
| | 0.05 | 35 | 10 |
| | 0.1 | 50 | 25-30 |
| | 0.5 | 60 | 30 |
| | 1.0 | 55-60 | 30-40 |
| Nitroglycerin | 0.5 | 20-25 | 0 |
| | 1.0 | 40-50 | 25-30 |

0 - absence of effect

In experiments on non-narcotized SHT rats intragastric administration of the compound of formula I has caused dose-dependent reduction of BP, the duration of which was increased correspondingly with dose increase (maximal duration of effect 5 hours after single administration of 50 mg/kg dose, Table 3).

The compound of formula I and arginine activate soluble guanylate cyclase of human platelets, and the activity of the compound I approaches that of L-arginine. The average degree of activation of the enzyme is 2.26 times when using L-arginine of 0.1 mM concentration, and 2.12 times when using the compound I of the same concentration (Table 4).

Compound I is non-toxic, well tolerated, causes practically no changes in general condition and behavior of animals, does not disrupt circadian rhythms and does not cause the reduction in food and water intake and weight loss. The compound does not disrupt CNS and does not exhibit neurotoxicity even in relatively high doses. Interaction with some pharmacological analyzers did not reveal any specific response from compound I. This, however, does not mean the absence of mediator mechanism of action.

TABLE 3

The effect of internal administration of the compound
of formula I and nitroglycerin on BP in non-narcotized
SHT rats (non-invasive BP measurement)

| Tested compound | Dose, mg/kg, orally | Reduction of BP, mmHg | | | | | |
|---|---|---|---|---|---|---|---|
| | | 1 | 2 | 3 | 4 | 5 | 6 |
| Compound I | 1 | 20* | 10 | 0 | 0 | 0 | 0 |
| | 5 | 17* | 20* | 32* | 30* | 15 | 0 |
| | 10 | 23* | 30* | 37 | 35 | 17* | 0 |
| | 25 | 26* | 32* | 45* | 45* | 25* | 0 |
| | 50 | 25* | 42* | 50* | 50* | 25* | 0 |
| Nitroglycerin | 10 | 0 | 0 | 0 | 0 | 0 | 0 |

*difference with base BP level is significant at $P < 0.05$
0 - absence of effect

TABLE 4

The effect of L-arginine and the compound of formula
I on specific activity of guanylate cyclase (GC,
pmol cGMP/min/mg protein) of human platelets

| Sample number | Initial specific activity of GC | Arginine (0.1 mmol) | | Compound I (0.1 mmol) | |
|---|---|---|---|---|---|
| | | Specific activity | Activation | Specific activity | Activation |
| 1 | 133 | 525 | 395 | 593 | 446 |
| 2 | 235 | 386 | 135 | 450 | 153 |
| 3 | 100 | 147 | 146 | 146 | 146 |
| 4 | 140 | 444 | 317 | 265 | 189 |
| 5 | 211 | 286 | 136 | 256 | 122 |
| Mean M ± m | 174 ± 33 | 358 ± 38 | 226 ± 54 | 342 ± 86 | 212 ± 67 |

Acute toxicity of the compound in mice in internal administration is 8.9±0.75 g/kg, cumulation after 28 days administration is weak (lethality less than 50%).

Therapeutic doses in animals do not exceed $1/100$ of $LD_{50}$ and are 4.0-8.0 and 12.0 mg/kg in intragastric administration.

A second object of the present invention is the method of production of the compound of formula I.

The title compound contains the following structural fragments: an indolinone ring, a cyano group in β-position of the side chain and a substituted cyclic fragment, in which attached to one carbon atom there are two strong electron donor groups—an ether oxygen atom and a substituted amino group. The inclusion of these groups in a cyclic system ensures the high level of coupling of their undivided electron pairs with double bonds of a side chain. This, together with a cyclic indole oxygen atom creates a system, that is similar to guanidine system in its electron parameters. This is of special interest, because it is known, that it is the guanidine fragment of arginine that is a source of nitric oxide in a living organism.

Method of producing the compound, a 2-[2-cyano-2-[5-(hydroxymethyl)-3-methyl-1,3-oxazolidin-2-ylidene]ethylidene]indolin-3-one of formula I, comprises the interaction of a [(3-acetoxyindol-2-yl)methylene]malononitrile (II) with 3-(methylamino)propane-1,2-diol (IIIa) in the medium of polar solvent (preferably, isopropyl alcohol) while boiling according to the following scheme:

SCHEME OF THE CLAIMED METHOD

We have earlier described the first case of non-catalytic addition of amines to a cyano group [2, 4, 5], comprising the interaction of the compound II with primary and secondary amines, including primary alkylamines, for example, 3-aminopropane-1,2-diol (IVa) [2, 4] in the medium of polar or non-polar solvent while boiling, producing the derivatives of 2-[2-cyano-3,3-diaminopropen-2-ylidene]indolin-3-one of general formula VIII according to Scheme 1:

Scheme 1 a R = OH; $R^1$ = $CH_2OH$
b R = H; $R^1$ = OH

As can be seen in Scheme 1, first the initial compound II is deacetylated (which requires 1 mol of 3-aminopropane-1,2-diol (IVa)). This deacetylation is accompanied by salt production (producing salt VIa) with the participation of intermediate compound V and amine IVa. Salt VIa dissociates when heated, and the released amine joins to the C≡N bond, producing amidine VIIa, which is in tautomeric balance with VIIIa [2, 4]. As our research has shown, the interaction of compound II with 2-aminoethanol (IVb) progresses similarly (Example A).

Synthesis and physical-chemical characteristics of 2-[3-amino-2-cyano-3-[(2,3-dihydroxypropyl)amino]propen-2-ylidene]indolin-3-one (VITA) are described in [2,4]. 1H NMR spectrum.

EXAMPLE A

2-[3-Amino-2-cyano-3-[(2-hydroxyethyl)amino]propen-2-ylidene]indolin-3-one (VIIIb)

A mixture of 2.5 g (10 mmol) of dicyanovinyl derivative II, 2.5 g (41 mmol) of 2-aminoethanol IVb and 100 ml of isopropyl alcohol is refluxed with stirring for 4 hours. The mixture is cooled, the solid is filtered and washed with isopropyl alcohol and diethyl ether. 1.67 g (yield 62%) of 2-[3-amino-2-cyano-3-[(2-hydroxyethyl)amino]propen-2-ylidene]indolin-3-one (VIIIb) is obtained. Melting point 209-210° C. (dec., DMF-$H_2O$ 4:1).

IRS, v, $cm^{-1}$: 3350, 3240-3060, 2190, 1670, 1605.

MS: $M^+$ 270.

Found, %: C, 62.14, H, 5.50, N, 20.73.

$C_{14}H_{14}N_4O_2$

Calc., %: C, 62.21, H, 5.22, N, 20.73.

¹H NMR

UV-Vis, $\lambda_{max}$, nm (Ig $\epsilon$): 217 (4.03), 231 (4.18), 257 (3.92), 286 (4.01), 310 (shoulder, 3.98), 379 (4.33), 490 (shoulder, 4.46), 509 (4.64).

Unexpected results were obtained after the interaction of compound II with N-substituted alkanolamines, such as 2-(methylamino)ethanol (IIIb) (Example B) and N-methylglucamine (IIIc) (Example C). At first, apparently, the interaction of compounds II and IIIb goes similarly to Scheme 1, however, the process does not stop at the stage of producing compounds of diendiamine structure of general formula VIII, instead, further oxazolidine cyclization with the release of ammonia molecule and production of derivatives of 2-[2-cyano-2-(3-methyloxazolidin-2-ylidene)ethylidene]indolin-3-one IX and X. Such oxazolidine cyclization is unexpected and unpredictable, and its necessary condition is the use of an N-substituted alkanolamine. Theoretically this factor is still unclear. Below is the scheme of production of compound IX and X.

IX R = H
X R = (CHOH)$_3$CH$_2$OH

EXAMPLE B

2-[2-Cyano-2-(3-methyloxazolidin-2-ylidene)ethylidene]indolin-3-one (IX)

A mixture of 2.5 g (10 mmol) of dicyanovinyl derivative II, 2.2 g (30 mmol) of 2-(methylamino)ethanol IIIb and 100 ml of isopropyl alcohol is refluxed with stirring for 3.5 hours. The mixture is cooled, the solid is filtered and washed with isopropyl alcohol and diethyl ether. 1.2 g (yield 44%) of 2-[2-cyano-2-(3-methyloxazolidin-2-ylidene)ethylidene]indolin-3-one (IX) is obtained. Melting point 222-226° C. (dec., DMF-MeOH 8:1).

IRS, $\nu$, cm$^{-1}$: 3350, 2200, 1675, 1600.

MS: M$^+$ 267.

Found, %: C, 67.61, H, 4.89, N, 15.96.

C$_{15}$H$_{13}$N$_3$O$_2$

Calc., %: C, 67.40, H, 4.90, N, 15.72; M, 267.

¹H NMR

UV-Vis, $\lambda_{max}$, nm (Ig $\epsilon$): 256 (shoulder, 3.96), 282 (4.09), 310 (shoulder, 4.03), 365 (4.36), 495 (4.41).

EXAMPLE C

2-[2-Cyano-2-[3-methyl-5-(1,2,3,4-tetrahydroxybutyl)oxazolidin-2-ylidene]ethylidene]indolin-3-one (X)

A mixture of 2.5 g (10 mmol) of dicyanovinyl derivative II, 4 g (20 mmol) of N-methylglucamine IIIc and 100 ml of isopropyl alcohol are refluxed with stirring for 3 hours. The mixture is cooled, the solid is filtered and washed with isopropyl alcohol and diethyl ether. 1.8 g (yield 45%) of 2-[2-cyano-2-[3-methyl-5-(1,2,3,4-tetrahydroxybutyl)oxazolidin-2-ylidene]ethylidene]indolin-3-one (X) is obtained. Melting point 237° C. (dec., DMF-H$_2$O 4:1).

IRS, $\nu$, cm$^{-1}$: 3430, 3320, 3180, 2190, 1650, 1600.

MS: 237 [M-OCH(CHOH)$_3$CH$_2$OH]$^+$, 210 [M-CH$_3$NCH$_2$CH(CHOH)$_3$CH$_2$OH]$^+$.

Found, %: C, 59.02, H, 5.47, N, 10.65.

C$_{19}$H$_{21}$N$_3$O$_6$

Calc., %: C, 58.91, H, 5.46, N, 10.85; M, 387.

¹H NMR

UV-Vis, $\lambda_{max}$, nm (Ig $\epsilon$): 220 (3.85), 255 (shoulder, 3.65), 282 (3.81), 310 (shoulder, 3.73), 369 (4.07), 497 (4.13).

Thus, the originality, singularity and unpredictability of producing compound I in the aforementioned conditions consists in that, up to now, cyclization of such type (with ammonium release) in the series of coupled diendiamines was not known, and such ring closing is unexpectedly made possible by the presence of a substitute on a nitrogen atom of the used alkanolamine.

The following example 3 illustrates the claimed method of production of the new compound I.

EXAMPLE 3

2-[2-Cyano-2-[5-(hydroxymethyl)-3-methyl-1,3-oxazolidin-2-ylidene]ethylidene]indolin-3-one (I)

A mixture of 2.5 g (10 mmol) of dicyanovinyl derivative II, 2.1 g (20 mmol) of 3-(methylamino)propane-1,2-diol IIIa and 100 ml of isopropyl alcohol are boiled while stirring for 2 hours. The mixture is cooled, the solid is filtered and washed with isopropyl alcohol and diethyl ether. 1.55 g (yield 52%) of 2-[2-cyano-2-[5-(hydroxymethyl)-3-methyl-1,3-oxazolidin-2-ylidene]ethylidene]indolin-3-one (I) is obtained. Melting point 236.5-237.5° C. (dec., DMFA-$H_2O$ 2:1).

IRS, ν, $cm^{-1}$: 3360, 3200, 2180, 1650.
MS: $M^+$ 297.
Found, %: C, 64.93, H, 5.11, N, 14.26.
$C_{16}H_{15}N_3O_3$
Calc., %: C, 64.63; H, 5.09, N, 14.13; M. 297.
$^1$H NMR, (DMSO-$d_6$, δ, ppm, J Hz): 3.94 (2H, t, $J_1=J_2=9.5$, $CH_2OH$), 3.96 (2H, q, $J_1=7.0$, $J_2=9.5$, $CH_2OH$), 5.33. (1H, t, $J_1=J_2=6.0$, $CH_2OH$), 3.54-3.80 (2H, m, 4"-$CH_2$), 4.91 (1H, oct, 5"-CH), 3.32 (3H, s, N-Me), 6.70 (1H, α-CH), 6.82, 7.22, 7.42, 7.54 (4H, m, H(4-7)), 8.44 (1H, s, N(1)H).

In the $^{13}$C NMR (DMSO-$d_6$) spectrum of compound I observed of aromatic carbon signals C(4-7) at 113.2, 118.5, 123.2 and 134.2 ppm, quaternary aromatic C-atoms at 121.1 and 151.4 ppm, C(1')-113.2, CN-120.1, C(2')-55.5, C(2")-166.2, N(3")Me-34.3, C(4")-53.3, C(5")-80.0 (d, J=156.3 Hz) and $CH_2OH$ at 61.0 ppm.

UV-Vis, $λ_{max}$, nm (lg ε): 222 (4.09), 257 (3.95), 284 (4.07), 310 (shoulder, 4.00), 368 (4.34), 497 (4.40).

Synthesis of the initial compound II is described in [23, 24] (Scheme 3).

Interaction of N-acetylindoxyl (XI) with N,N-dimethylformamide diethyl acetal gives enaminoindolinone-3 XII, which is hydrolyzed by acid in situ to 1-acetyl-2-formyl-3-hydroxyindole (XIII) (yield~60÷70%). It should be noted that C(1')-C(2) bond of aldehyde is easily broken, and lengthening the duration of treatment of the intermediate compound XII with diluted HCl produces N-acetylindoxyl XI [1]. 2-Formylindole XIII is a highly labile compound that can't withstand long-term storage, so in order to perform reactions of this compound's formyl group with CH-acids it is first necessary to transform it into 3-acetoxy-1-acetyl-2-formylindole (XIV) as fast as possible. The reaction of compound XIV with malononitrile in benzene in the presence of triethylamine produces dicyanovinylindole II. The examples below illustrate the method of synthesizing the initial compound II according to Scheme 3 [1,3]:

1-Acetyl-2-formyl-3-hydroxyindole (XIII) [1]. 198 ml (~1.24 mol) of DMF diethyl acetal is added into a suspension of 56 g (0.32 mol) indoxyl XI in 640 ml of benzene and stirred for 1 hour at 20° C. The resulting solution is refluxed for 1 hour. Benzene is evaporated in vacuo, with bath temperature less than 60° C. After evaporating benzene, the residue is dissolved in ~4 liters of water and acidified (pH 2-3) by 60 ml of conc. HCl. After 5 min the solid is filtered and washed with water and isopropyl alcohol. 45.5 g (yield 70%) of compound XIII is obtained. Melting point 122-123° C. (from isopropyl alcohol).

IRS, ν, $cm^{-1}$: 1700, 1620, 1580.
MS: $M^+$ 203.
Founs, %: C, 64.73, H, 4.50, N, 6.90.
$C_{11}H_9NO_3$.
Calc., %: C, 65.02, H, 4.47, N, 6.89.
$^1$H NMR (CDCl$_3$, δ, ppm): 10.24 (1H, br. s, CHO); 2.79 (3H, s, NCOCH$_3$); 7.34-7.91 (4H, m, Ar).
UV-Vis, $λ_{max}$, nm (lg ε): 230 (4.22), 257 (4.03), 312 (3.95), 356 нм (3.89).

3-Acetoxy-1-acetyl-2-formylindole (XIV) [1]. A solution of 45.5 g (0.23 mol) of aldehyde of XIII in 130 ml of acetic anhydride is refluxed for 10 minutes. It is cooled, the solid is filtered, washed with acetic anhydride and diethyl ether. 31.8 g (yield 58%) of compound XIV is obtained. Melting point 111-113° C. (ethyl acetate).

IRS, ν, $cm^{-1}$: 1785, 1700, 1670, 1610.
MS: $M^+$ 245.
Found, %: C, 63.66, H, 4.52, N, 5.64.
$C_{13}H_{11}NO_4$
Calc., %: C, 63.67, H, 4.52, N, 5.71.
$^1$H NMR (Me$_2$CO-$d_6$, δ, ppm): 10.15 (1H, s, CH); 2.45 (3H, s, OCOCH$_3$); 2.48 (3H, s, NCOCH$_3$); 7.38-8.12 (4H, m, Ar).

A nitrile of α-cyano-β-(3-acetoxyindolyl-2)acrylic acid (II) [3]. 14.4 ml (0.1 mol) of triethylamine and 7.8 g (0.12 mol) malondinitrile are added to a solution of 24.4 g (0.1 mol) of 2-formylindole XIV in 500 ml of benzene, while stirring continuously, at 20° C. (external water cooling). The mixture is stirred for 1.5-2 hours. The residue is filtered, rinsed with benzene and methanol. 22.7 g (yield 90%) of nitrile II is obtained. Melting point 210-212° C. (decomp. from acetone).

IRS, ν, $cm^{-1}$: 3340, 2240, 2230, 1770, 1600.
MS: $M^+$ 251.
Found, %: C, 67.07, H, 3.42, N, 16.63.
$C_{14}H_9N_3O_2$.
Calc., %: C, 66.93, H, 3.61, N, 16.73.
$^1$H NMR (Me$_2$CO-$d_6$, δ, ppm): 2.47 (3H, s, OCOCH$_3$); 8.17 (1H, s, CH); 10.39 (1H, s, NH); 7.19-7.68 (4H, m, Ar).

Scheme 3

¹³C ЯMP (DMSO-d₆+CD₃OD, δ, ppm): 168.5 (q, J≈7 Hz, OCOCH₃); 20.7 (q, J=142 Hz, OCOCH₃); 114.9 (d, J=8.1 Hz, CN); 113.8 (d, J=13.5 Hz, CN); 74.4 (d, J=2 Hz, a-C); 144.3 (d, J=166 Hz, β-CH); 138.8; 138.4 (m, C (2), C (7a)); 119.4 (m, C (3a)); 121.4 (d, J=2 Hz, C (3)); 128.3, 121.4, 119.8, 113.9 (q, J1=160 . . . 165 Hz, J≈8 Hz, C (4), C (5), C (6), C (7)).

Yield of 2-[2-cyano-2-[5-(hydroxymethyl)-3-methyl-1,3-oxazolidin-2-ylidene]ethylidene]indolin-3-one (1), calculating for N-acetylindoxyl according to Scheme 3, is 13.5% (accounting for the recrystallization of the target product).

A weakness of this method of synthesis of compound II is the synthesis of 2-formylindole XIII, to wit, the hydrolysis operation, which must be carried out in a strictly determined time frame. It is clear that, when scaling up the process, there exists a possibility of contamination of 2-formylindole XIII by a product of its subsequent hydrolysis-1-acetylindoxyl, or producing pure 1-acetylindoxyl. For this reason, in order to avoid technological difficulties, associated with the production of intermediate 2-formylindole XIII during scaling up the process, we have modified the synthesis scheme of II (Scheme 4):

The goal is achieved by the claimed method of producing the compound II, a key intermediate product for synthesizing the biologically active compound I.

Synthesis of the initial compound II according to Scheme 4 begins, similarly to Scheme 3, with the interaction of N-acetylindoxyl with acetal of DMF, however, after this, unlike Scheme 3, comes the deacetylation of the intermediate enaminoketone XII by triethylamine in methanol, producing enaminoketone XV with 55% yield [1]. We have described the acylation of enaminoketone XV [3] with different acyl halides. Unlike method [3], which describes the acetylation of enaminoketone XV in acetyl chloride medium, we have performed the acetylation in DMFA medium. As a result, the produced 3-acetoxy-2-[(dimethylimino)methyl]indole chloride (XVI) after being dissolved in water is converted into 3-acetoxy-2-formylindole (XVII) with 63% yield, compared to 25% in method [3]. The reaction of 3-acetoxy-2-formylindole (XVII) with malononitrile in benzene in the presence of triethylamine produces dicyanovinylindole II with high yield. Example 4 and 5 below illustrate the method of synthesis of the initial compound II according to Scheme 4.

2-[(Dimethylamino)methylen]indolin-3-one (XV) [1] is produced from 7 g (40 mmol) of indoxyl XI and 24 ml (120 mmol) of acetal of DMF in 80 ml of benzene in the same synthesis conditions as those of the compound XIII. After evaporating of benzene, the residue is dissolved in 60 ml of methanol, 6 ml of triethylamine is added and the mixture is refluxed for 30 minutes. Methanol is evaporated. The residue is mixed with ethylacetate, the precipitate is filtered and washed with isopropyl alcohol and diethyl ether. XV yield is 41 g (55%). Melting point 215° C. (dec., isopropyl alcohol).

IRS, ν, cm⁻¹: 3250-3100, 1675, 1615.
MS: M⁺ 188.
Found, %: C, 70.33, H, 6.44, N, 14.94.
$C_{11}H_{12}N_2O$.
Calc., %: C, 70.19, H, 6.43, N, 14.88.
¹H NMR, (DMSO-d₆, δ, ppm): 7.01 (1H, s, CH); 6.78-7.31 (4H, m, Ar); 3.19, 3.35 (6H, both s, N (CH₃)₂); 8.85 (1H, s, NH).
UV-Vis, λ_max, nm (Ig ε): 254 (4.05), 290 (4.03), 338 (4.32), 437 HM (4.12).

EXAMPLE 4

3-Acetoxy-2-formylindole (XVII). 0.31 ml (4.4 mmol) of acetyl chloride is added dropwise, while stirring continuously and cooling with water, to a suspension of 0.38 g (2 mmol) of enaminoketone XV [1] in 2.5 ml DMF. The mixture is stirred at room temperature for 5 hours. After 2 hours another 0.31 ml of acetyl chloride is added. The mixture is stored in refrigerator (5-7° C.) overnight. The residue is filtered, rinsed with DMFA and acetone. 0.4 g (yield 75%) of 3-acetoxy-2-[(dimethylimino)methyl]indole chloride (XVI) is obtained, which is then dissolved in 25 ml of water and cooled with ice for 15 min. The residue is filtered, washed with water and dried. 0.26 g (yield 63%) of 3-acetoxy-2-formylindole (XVII) is obtained. Melting point 145-147° C. (water-isopropyl alcohol 5:1). Melting point of mixture of the compound with a sample of the compound, produced using method [3], does not decrease.

IRS, ν, cm⁻¹: 3280, 1770, 1660, 1620.
MS: M⁺ 203.
Found, %: C, 65.04, H, 4.64, N, 6.76.
$C_{11}H_9NO_3$.
Calc., %: C, 65.02, H, 4.47, N, 6.89.
¹H NMR, (CDCl₃, δ, ppm): 9.90 (1H, s, CHO), 9.17 (1H, br. s, NH), 7.12-7.57 (4H, m, Ar), 2.48 (3H, s, OCOCH₃).

EXAMPLE 5

A [(3-acetoxyindol-2-yl)methylene]malononitrile (II). 0.01 ml (0.072 mmol) of triethylamine and 0.05 g (0.72 mmol) malononitrile are added, with stirring continuously at 20° C. (external water cooling), into a solution of 0.15 g (0.6 mmol) of 2-formylindole XVII in 5 ml of benzene. The mixture is stirred for 0.5 hours. The solid is filtered and washed with benzene and methanol. 0.15 g (yield 99%) of the nitrile II is obtained. Melting point 210-212° C. (dec., acetone). Melting point of mixture of the compound with a sample of the compound, produced using method [7], does not decrease.

Yield of 2-[2-cyano-2-[5-(hydroxymethyl)-3-methyl-1,3-oxazolidin-2-ylidene]ethylidene]indolin-3-one (I), calculating for N-acetylindoxyl according to Scheme 4, is 12.5% (accounting for the recrystallization of the target product).

The methods of synthesizing the title compound, 2-[2-cyano-2-[5-(hydroxymethyl)-3-methyl-1,3-oxazolidin-2-ylidene]ethylidene]indolin-3-one (I), from the nitrile II according to Schemes 3 and 4, that we developed, allow to produce this compound with approximately equal yields (13.5-12.5%). Scheme 4 has certain technological advantages over Scheme 3, however, both schemes require the use of high quantity of an expensive and not readily available reagent—diethyl acetal of dimethylformamide. In order to avoid the use of an expensive reagent—diethyl acetal of dimethylformamide—and also to increase the yield of the desired product I, we have set a goal to develop an alternative approach to synthesizing the compound I.

The goal is achieved by the claimed method of producing 2-[2-cyano-2-[5-(hydroxymethyl)-3-methyl-1,3-oxazolidin-2-ylidene]ethylidene]indolin-3-one (Scheme 5), comprising the interaction of N-acetylindoxyl (XI) with (ethoxymethylene)malononitrile (XVIII), producing [(1-acetyl-3-hydroxyindol-2-yl)methylene]malononitrile (XIX), which is then acetylated by acetic anhydride, producing [(3-acetoxy-1-acetylindol-2-yl)methylene]malononitrile (XX). The latter is interacted with equimolecular amount of 3-(methylamino)propane-1,2-diol (IIIa), converting to previously unknown 1-acetyl-2-[2-cyano-2-(5-hydroxymethyl-3-methyloxazolidin-2-ylidene)ethylidene]indolin-3-one (XXI). Acetyl group is removed by Triton B (benzyltrimethylammonium hydroxide, 40% solution in methanol) in methanol, producing the title compound I.

Scheme 5

Examples 6-8 below illustrate the method of synthesizing the title compound I according to Scheme 5.

EXAMPLE 6

[(3-acetoxy-1-acetylindol-2-yl)methylene]malononitrile (XX). 39.04 g (0.32 mol) of (ethoxymethylene)malononitrile (XVIII) is added to a suspension of 56 g (0.32 mol) of N-acetylindoxyl in 80 ml of pyridi[(3-Acetoxy-1-acetylindol-2-yl)methylene]malononitrile ne. Then, 44.8 ml (0.32 mol) of triethylamine is added, with stirring and cooling with water, the temperature of the reaction mixture is 25±2° C. The mixture is stirred at this temperature for 1 hour, then [(1-acetyl-3-hydroxyindol-2-yl)methylene]malononitrile (XIX) is precipitated by 160 ml of acetic anhydride while cooling on ice bath. The temperature of the reaction mixture less than 30° C. After keeping the mixture for 1 hour at 20° C. the solid is filtered and washed with acetic anhydride and acetone. Product dried on air for 1 hour. 79.6 g of [(1-acetyl-3-hydroxyindol-2-yl)methylene]malononitrile (XIX) is obtained. 500 ml of acetic anhydride is the added to it, the mixture is refluxed for 30 minutes, with vigorously stirring. The mixture is cooled, the solid is filtered, washed with acetic anhydride and acetone and dried to constant weight. 65.34 g (yield 69.6%) of [(3-acetoxy-1-acetylindol-2-yl)methylene]malononitrile (XX) is obtained. Melting point 250-252° C. (dec., acetic anhydride).

IRS, ν, cm$^{-1}$: 2225, 1692, 1655, 1607.
MS: M$^+$ 293.
Found, %: C, 65.44, H, 3.42, N, 14.12.
$C_{16}H_{11}N_3O_3$.
Calc., %: C, 65.52, H, 3.78, N, 14.33.
$^1$H NMR, (DMSO-d$_6$, δ, ppm): 2.32 (3H, s, OCOCH$_3$), 2.85 (3H, s, NCOCH$_3$), 7.48 (1H, t, H(5)), 7.68 1H, t, H(6)), 7.85 (1H, d, H(4)), 8.25 (1H, d, H(7)), (8.90 (1H, s, H(2')).

EXAMPLE 7

1-Acetyl-2-[2-cyano-2-(5-hydroxymethyl-3-methyloxazolidin-2-ylidene)ethylidene]indolin-3-one (XXI). A mixture of 66.18 g (0.226 mol) of [(3-acetoxy-1-acetylindol-2-yl)methylene]malononitrile (XX), 47.5 g (0.452 mol) of 3-(methylamino)propane-1,2-diol (VIIIa) and 1400 ml isopropyl alcohol is refluxed, with stirring, for 1 hour. The mixture is cooled, the solid is filtered, washed with isopropyl alcohol and dried at 80° C. 66.4 g (yield 86.7%) of 1-acetyl-2-[2-cyano-2-(5-hydroxymethyl-3-methyloxazolidin-2-ylidene)ethylidene]indolin-3-one (XXI) is obtained. Melting point 218-220° C. (methanol).

IRS (KBr), ν, cm⁻¹: 2220, 1700, 1680, 1610.
MS: M⁺ 339.
Found, %: C, 63.71, H, 5.01, N, 12.37. $C_{18}H_{17}N_3O_4$.
Calc., %: C, 63.71, H, 5.05, N, 12.38.
¹H NMR, (DMSO-$d_6$, δ, ppm, J Hz): 2.42 (3H, s, NCOCH₃), 3.39 (3H, s, N(3")Me), 3.98 (2H, t, $J_1=J_2=9.5$, CH₂OH), 3.80 (2H, q, $J_1=7$, $J_2=9.5$, CH₂OH), 5.19 (1H, t, $J_1=J_2=6$, CH₂OH), 3.55-3.90 (2H, m, 4'-CH₂), 4.94 (1H, oct, 5'-CH), 7.20 (1H, H(1)'), 6.82, 7.23 (1H, d, H(4)), 7.59-7.67 (2H, m, H(5-6)), 8.07 ((1H, d, H(7)).

EXAMPLE 8

2-[2-Cyano-2-[5-(hydroxymethyl)-3-methyl-1,3-oxazolidin-2-ylidene]ethylidene]indolin-3-one (I). 115.7 ml (0.254 mol) of Triton B is added to a suspension of 66.4 g (0.196 mol) 1-acetyl-2-[2-cyano-2-(5-hydroxymethyl-3-methyloxazolidin-2-ylidene)ethylidene]indolin-3-one (XXI) in 800 ml of methanol and stirred at 20° C. for 30 min. The solid is filtered, washed with methanol, water and methanol. Product dried at 80° C., obtaining 40.6 g (yield 69.7%) of 2-[2-cyano-2-[5-(hydroxymethyl)-3-methyl-1,3-oxazolidin-2-ylidene]ethylidene]indolin-3-one (I). It is recrystallized from 650 ml of DMF-water mixture, 2:1. 35.7 g of pure compound I is obtained. Melting point of mixture of the compound with samples of compounds, produced according to Schemes 3 and 4, does not decrease.

IR-, mass-, NMR, UV-Vis spectra and polarograms of sample of the compound I, produced according to Schemes 3, 4 and 5 are identical.

Conclusion: Effective methods of synthesizing a novel biologically active compound—2-[2-cyano-2-[5-(hydroxymethyl)-3-methyl-1,3-oxazolidin-2-ylidene]ethylidene]indolin-3-one (I)—have been developed.

REFERENCES

1. Ryabova S. Y., Trofimkin Y. I., Alexeeva L. M., Bogdanova G. A., Sheinker Y. N., Granik V. G.//Chemistry of Heterocyclic Compounds. 1990. No 11. P. 1487-1494.
2. Ryabova S. Y., Alexeeva L. M., Granik V. G., Faermark I. F., Shvarts G. Y. Patent RU2008308 "Indolin-3-one derivatives with antihypertensive activity and process for preparation thereof".
3. Ryabova S. Y., Trofimkin Y. I., Alexeeva L. M., Habarova L. S., Granik V. G.//Chemistry of Heterocyclic Compounds. 1991. No 3. P. 343-348.
4. Ryabova S. Y., Trofimkin Y. I., Granik V. G., Faermark I. F., Shvarts G. Y., Patent RU2026287 "Derivatives of pyrroline-2-one-4 or indolinone-3 showing antihypertensive activity and a method of their synthesis".
5. Ryabova S. Y., Trofimkin Y. I., Alexeeva L. M., Kerbnikova I. F., Shvarts G. Y., Granik V. G.//Chem.-Pharm. Journal. 1995. T. 29 (9). P. 22-29.
6. Khmelnitzkaya E. Y., Grigoriev N. B., Ryabova S. Y., Trofimkin Y. I., Azimov V. A., Granik V. G.//Chemistry of Heterocyclic Compounds. 2002. No 11. P. 1540-1546.
7. Feelish M.//J. Cardiovascular. Pharm. 1991. Vol. 17 (Suppl 3). P. 25.
8. Hansson G. K.//Atheroscler. Thromb. Vasc. Biol. 2001. Vol. 21(12). P. 1876.
9. Orekhov A. N., Tertov V. V., Pivovarova E. M.//Cardiology. 1998. Vol. 89. P. 111.
10. Zadelaar S., Kleemann R., Verschuren L., et al.//Atheroscler. Thromb. Vasc. Biol. 2007. Vol. 27. P. 1706.

The invention claimed is:
1. A method of using a medicinal preparation comprising the compound 2-[2-cyano-2-[5-(hydroxymethyl)-3-methyl-1,3-oxazolidin-2-ylidene]ethylidene]indolin-3-one of formula I as a platelet aggregation inhibitor and an antihypertensive agent for the treatment of cardiovascular diseases in a mammal by administering therapeutically effective doses of the compound to a mammal.

2. A method of claim 1, wherein the medicinal preparation is suitable for oral, parenteral, sublingual or administration.